United States Patent [19]

Yu et al.

[11] Patent Number: 5,506,133
[45] Date of Patent: Apr. 9, 1996

[54] SUPEROXIDE DISMUTASE-4

[75] Inventors: Gu-Liang Yu, Darnestown; Craig A. Rosen, Laytonsville; Claire M. Fraser, Queenstown; Jeannine D. Gocayne, Silver Spring, all of Md.

[73] Assignee: Human Genome Sciences, Inc., Rockville, Md.

[21] Appl. No.: 225,757

[22] Filed: Apr. 11, 1994

[51] Int. Cl.$^6$ .............. C12N 1/21; C12N 5/10; C12N 15/53; C12N 15/63

[52] U.S. Cl. .............. 435/240.2; 536/23.2; 435/252.3; 435/254.11; 435/320.1

[58] Field of Search .............. 536/23.2; 435/320.1, 435/240.2, 252.3, 189

[56] References Cited

U.S. PATENT DOCUMENTS

| | | | |
|---|---|---|---|
| 4,976,959 | 12/1990 | Berger et al. | 424/94.2 |
| 5,242,794 | 9/1993 | Whiteley et al. | 435/6 |
| 5,248,603 | 9/1993 | Marklund et al. | 435/189 |
| 5,252,476 | 9/1993 | Hallewell et al. | 435/189 |

FOREIGN PATENT DOCUMENTS 4-108379  4/1992  Japan.

OTHER PUBLICATIONS

Danciger et al., Proc. Natl. Acad. Sci. USA 83:3619–3623 (1986).
Chem. Abstracts 118(10):87658x (1993).
Chem. Abstracts 118(8):66893e (1993).
Chem. Abstracts 118(3):18538w (1993).
Chem. Abstracts 114(7):60461h (1991).
Chem. Abstracts 111(15):129816k (1989).
Chem. Abstracts 107(25):234823q (1987).
Chem. Abstracts 110(3):18553g (1989).

*Primary Examiner*—Robert A. Wax
*Assistant Examiner*—Eric Grimes
*Attorney, Agent, or Firm*—Elliot M. Olstein; Gregory D. Ferraro

[57] ABSTRACT

Polynucleotides which encode the polypeptide SOD-4, as well as such polypeptides, and antibodies against the polypeptide and the use of the polypeptide as a pharmaceutical for treating cerebral ischaemia, ulcers, inflammation, arrhythmia, oedema and paraquat intoxication as well as rheumatoid arthritis, osteoarthritis and radiation injury.

36 Claims, 4 Drawing Sheets

```
  1 CTGGTTGGTGCTCCTGCGCCGGAGGAGTTCTGCGTCTCGGGGTGGTGACTGGGTCCAGAA   60
 61 TGGCTTCGGATTGGGGAACaGGGGACCCTCTGCACGTTGGAGTTCGCGGTGCAGATGACC  120
                                                           M  T

121 TGTCAGAGCTGTGTGGACGCGGTGCGCAAATCCCTGCAAGGGGTGGCAGGTGTCCAGGAT  180
     C  Q  S  C  V  D  A  V  R  K  S  L  Q  G  V  A  G  V  Q  D

181 GTGGAGGTGCACTTGGAGGACCAGATGGTCTTGGTACACACCACTCTACCCAGCCAGGAG  240
     V  E  V  H  L  E  D  Q  M  V  L  V  H  T  T  L  P  S  Q  E

241 GTGCAGGCTCTCCTGGAAGGCACGGGGCGGCAGGCGGTACTCAAGGGCATGGGCAGCGGC  300
     V  Q  A  L  L  E  G  T  G  R  Q  A  V  L  K  G  M  G  S  G

301 CAGTTGCAGAATCTGGGGGCAGCAGTGGCCATCCTGGGGGGGGCTGGCACCGTGCAGGGG  360
     Q  L  Q  N  L  G  A  A  V  A  I  L  G  G  A  G  T  V  Q  G

361 GTGgTGCGCTTCCTACAGcTGACCCcTGAGCGCTGCcTCATCGAGGGAAcTATTGACGGC  420
     V  V  R  F  L  Q  L  T  P  E  R  C  L  I  E  G  T  I  D  G

421 CTGGAGCCTGGGCTGCATGGACTCCACGTCCATCAGTACGGGGACCTTACAAACAACTGC  480
     L  E  P  G  L  H  G  L  H  V  H  Q  Y  G  D  L  T  N  N  C

481 AACAGCTGTGGGAATCACTTTAACCCTGATGGAGCATCTCATGGGGGCCCCCAGGACTCT  540
     N  S  C  G  N  H  F  N  P  D  G  A  S  H  G  G  P  Q  D  S

541 GACCGGCACCGcGGAGACCTGGGCAATGTCCGTGCTGATGCTGACGGCCGCGCCATCTTC  600
     D  R  H  R  G  D  L  G  N  V  R  A  D  A  D  G  R  A  I  F

601 AGAATGGAGGATGAGCAGCTGAAGGTGTGGGATGTGATTGCCCGCAGCCTGATTATTGAT  660
     R  M  E  D  E  Q  L  K  V  W  D  V  I  A  R  S  L  I  I  D

661 GAGGGAGAAGATGACCTGGGCCGGGGAGGCCATCCCTTATCCAAGATCACAGGGAACTCC  720
     E  G  E  D  D  L  G  R  G  G  H  P  L  S  K  I  T  G  N  S

721 GGGGAGAGGTTGGCCTGTGGCATCATTGCACGCTCCGCTGGCCTTTTCCAGAACCCCAAG  780
     G  E  R  L  A  C  G  I  I  A  R  S  A  G  L  F  Q  N  P  K

781 CAGATCTGCTCTTGCGATGGCCTCACCATCTGGGAGGAGCGAGGCCGGCCCATCGCTGGC  840
     Q  I  C  S  C  D  G  L  T  I  W  E  E  R  G  R  P  I  A  G

841 AAGGGCCGAAAGGAGTCAGCGCAGCCCCCTGCCCACCTTTGAGCAGGACCTCACCTTGGC  900
     K  G  R  K  E  S  A  Q  P  P  A  H  L

901 TCTGTTGCTGTCCTCCAGGGCGAGCACTTTCCACTTCCAGAGGGGGCCAGAGGGACTTTG  960
961 CTTGCCCAGTCTTTGGAGAGCTCAGTACAGGGCAGGAGCTGCTGTGGTGTTCCCTTGGCA 1020
1021 AATGAAAGTTTTATTTTCGTTTGGGAAAAAAAAAAAAAAAAAAAAAAAAAAAAAAAAAAA 1080
```

FIG.1

```
              1         10        20        30        40        50        60        70        80
Human SOD4    GAAVAILGGAGTVQGVVRFLQLTPE.RCLIEGTIDGLEPGLHGLHVHQYGDLTNNCNSCGNHFNPDGASHGGPQDSDRHR
Schistosome   MK--CVMT-TAG-K---K-T-E-DNGPVHVHAEFS--KA-K-F---EF--T--G-T-A-A---TKQE--A-E--I---V
Bovine        TK--CV-K-D-P-Q-TIH-EAKG.D.TVVVT-S-T--TE-D--F----F--N-QG-T-A-P---LSKK---K-EE--V
Cauliflower   AKG-CV-NSSEG-K-TIF-THEGNG.ATTVT-VS--R-----F---AL--N--G-M-T-P----KT--A-E-AN--A
Drosophila    VK--CVIN..DAK-T-F-E-ESSGTPVKVS-EVC--AK---F---EF--N--G-M-S-P---Y-KE--A-V-EN--L
Human SOD1    TK--CV-K-D-P---IIN-E-KESNGPVKVW-S-K--TE---F---EF--N-AG-T-A-P---LSRK---K-EE--V
Tomato        VK--CV-NSSEG-S-TYL-T-VGVA.PTTVN-N-S--K-----F---AL--N--G-M-T-P-Y--A-KE--A-E-EV--V
Maize         VK---V-A-TD.-K-TIF-S-EGDG.PTTVT-S-S--K-----F---AL--T--G-M-T-P----V-KE--A-E-E---A
Mouse         MK--CV-K-D-P---TIH-E-KASG.EPWLS-Q-T--TE-Q--F----N-QG-T-A-P---HSKK---A-EE--V
Xenopus       VK--CV-A-S-D-K---R-E-QDDG.DVTV--K-E--TD-N--F-I-VF--N--G-L-A-P---QNKN--S-K-A--V
S.cerevisiae  VQ--AV-K-DAG-S---K-E-ASESEPTTVSYE-A-NS-NAERF-I-EF--A--G-V-A-P---FKKT--A-T-EV--V 81        90        100       110       120       130       140       150
Human SOD4    GDLGNVRADADGRAIFRMEDEQLKVWD...VIARSLIIDEGEDDLGRGGHPLSKITGNSGERLACGIIARSAG
Schistosome   ------V-G---N-VYNAT-KLISLNGSHSI-G--MV-H-N------E---V--A-G----VVGLA-E
Bovine        ------T--KN-V--VDIV-PLISLSGEYSI-G-TMVVH-KP-----NEE-TK--A-S----V-GIIK.
Cauliflower   ------IIVGD--T-T-TIT-S-IPLSGPNSIVG-AIVVHADP---K--E--LS--A-G-V----GIQG.
Drosophila    ------IE-TG-CPTKVNIT-SKITLFGADSI-G-TVVVHADA---Q--E--S--A-A-IG--V-GIIKV
Human SOD1    ------T--K--V-DVSI--SVISLSGDHCI-G-T--VVH-KA---K-NEE-TK--A-S----V-GIIQ.
Tomato        ------ITVGE--T-S-TIT-K-IPLTGPQSI-G-AVVVHADP---K--E---S--A-G-I----GIQG.
Maize         ------T-GE--VVNVNIT-S-IPLAGPHSI-G-AVVVHADP---K--E---S--A-G-V----GIQG.
Mouse         ------T-GK--V-NVSI--RVISLSGEHSI-G-TMVVH-KQ----K-NEE-TK--A-S----V-GIIQ.
Xenopus       ------T-E.G-V-Q-NFT-P-ISLKGERSI-G-TAVVH-KQ----K--DDE-LK---A-G----V-GFCP.
S.cerevisiae  --M--KT-EN-V-KGSFK-SLI-LIGPTS-VG--VV-HA-Q----K-DTEE-LK---A-P-P--VIGITN.
```

FIG.2

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
( A ) LENGTH: 1080 BASE PAIRS
( B ) TYPE: NUCLEIC ACID
( C ) STRANDEDNESS: SINGLE
( D ) TOPOLOGY: LINEAR ( i i ) MOLECULE TYPE: cDNA ( x i ) SEQUENCE DESCRIPTION: SEQ ID NO:1:

```
CTGGTTGGTG  CTCCTGCGCC  GGAGGAGTTC  TGCGTCTCGG  GGTGGTGACT  GGGTCCAGAA     60
TGGCTTCGGA  TTGGGGAACA  GGGGACCCTC  TGCACGTTGG  AGTTCGCGGT  GCAGATGACC    120
TGTCAGAGCT  GTGTGGACGC  GGTGCGCAAA  TCCCTGCAAG  GGGTGGCAGG  TGTCCAGGAT    180
GTGGAGGTGC  ACTTGGAGGA  CCAGATGGTC  TTGGTACACA  CCACTCTACC  CAGCCAGGAG    240
GTGCAGGCTC  TCCTGGAAGG  CACGGGGCGG  CAGGCGGTAC  TCAAGGGCAT  GGGCAGCGGC    300
CAGTTGCAGA  ATCTGGGGGC  AGCAGTGGCC  ATCCTGGGGG  GGGCTGGCAC  CGTGCAGGGG    360
GTGGTGCGCT  TCCTACAGCT  GACCCCTGAG  CGCTGCCTCA  TCGAGGGAAC  TATTGACGGC    420
CTGGAGCCTG  GGCTGCATGG  ACTCCACGTC  CATCAGTACG  GGGACCTTAC  AAACAACTGC    480
AACAGCTGTG  GGAATCACTT  TAACCCTGAT  GGAGCATCTC  ATGGGGCCC  CCAGGACTCT    540
GACCGGCACC  GCGGAGACCT  GGGCAATGTC  CGTGCTGATG  CTGACGGCCG  CGCCATCTTC    600
AGAATGGAGG  ATGAGCAGCT  GAAGGTGTGG  GATGTGATTG  CCCGCAGCCT  GATTATTGAT    660
GAGGGAGAAG  ATGACCTGGG  CCGGGGAGGC  CATCCCTTAT  CCAAGATCAC  AGGGAACTCC    720
GGGGAGAGGT  TGGCCTGTGG  CATCATTGCA  CGCTCCGCTG  GCCTTTTCCA  GAACCCCAAG    780
CAGATCTGCT  CTTGCGATGG  CCTCACCATC  TGGGAGGAGC  GAGGCCGGCC  CATCGCTGGC    840
AAGGGCCGAA  AGGAGTCAGC  GCAGCCCCCT  GCCCACCTTT  GAGCAGGACC  TCACCTTGGC    900
TCTGTTGCTG  TCCTCCAGGG  CGAGCACTTT  CCACTTCCAG  AGGGGGCCAG  AGGGACTTTG    960
CCTGCCCAGT  CTTTGGAGAG  CTCAGTACAG  GGCAGGAGCT  GCTGTGGTGT  TCCCTTGGCA   1020
AATGAAAGTT  TTATTTTCGT  TTGGGAAAAA  AAAAAAAAAA  AAAAAAAAA   AAAAAAAAA   1080
```

( 2 ) INFORMATION FOR SEQ ID NO:2:

( i ) SEQUENCE CHARACTERISTICS:
( A ) LENGTH: 255 AMINO ACIDS
( B ) TYPE: AMINO ACID
( C ) STRANDEDNESS:

(D) TOPOLOGY: LINEAR (ii) MOLECULE TYPE: PROTEIN (xi) SEQUENCE DESCRIPTION: SEQ ID NO:2:

| Met | Thr | Cys | Gln | Ser | Cys | Val | Asp | Ala | Val | Arg | Lys | Ser | Leu | Gln |
|---|---|---|---|---|---|---|---|---|---|---|---|---|---|---|
|  |  |  |  | 5 |  |  |  |  | 10 |  |  |  |  | 15 |
| Gly | Val | Ala | Gly | Val | Gln | Asp | Val | Glu | Val | His | Leu | Glu | Asp | Gln |
|  |  |  |  | 20 |  |  |  |  | 25 |  |  |  |  | 30 |
| Met | Val | Leu | Val | His | Thr | Thr | Leu | Pro | Ser | Gln | Glu | Val | Gln | Ala |
|  |  |  |  | 35 |  |  |  |  | 40 |  |  |  |  | 45 |
| Leu | Leu | Glu | Gly | Thr | Gly | Arg | Gln | Ala | Val | Leu | Lys | Gly | Met | Gly |
|  |  |  |  | 50 |  |  |  |  | 55 |  |  |  |  | 60 |
| Ser | Gly | Gln | Leu | Gln | Asn | Leu | Gly | Ala | Ala | Val | Ala | Ile | Leu | Gly |
|  |  |  |  | 65 |  |  |  |  | 70 |  |  |  |  | 75 |
| Gly | Ala | Gly | Thr | Val | Gln | Gly | Val | Val | Arg | Phe | Leu | Gln | Leu | Thr |
|  |  |  |  | 80 |  |  |  |  | 85 |  |  |  |  | 90 |
| Pro | Glu | Arg | Cys | Leu | Ile | Glu | Gly | Thr | Ile | Asp | Gly | Leu | Glu | Pro |
|  |  |  |  | 95 |  |  |  |  | 100 |  |  |  |  | 105 |
| Gly | Leu | His | Gly | Leu | His | Val | His | Gln | Tyr | Gly | Asp | Leu | Thr | Asn |
|  |  |  |  | 110 |  |  |  |  | 115 |  |  |  |  | 120 |
| Asn | Cys | Asn | Ser | Cys | Gly | Asn | His | Phe | Asn | Pro | Asp | Gly | Ala | Ser |
|  |  |  |  | 125 |  |  |  |  | 130 |  |  |  |  | 135 |
| His | Gly | Gly | Pro | Gln | Asp | Ser | Asp | Arg | His | Arg | Gly | Asp | Leu | Gly |
|  |  |  |  | 140 |  |  |  |  | 145 |  |  |  |  | 150 |
| Asn | Val | Arg | Ala | Asp | Ala | Asp | Gly | Arg | Ala | Ile | Phe | Arg | Met | Glu |
|  |  |  |  | 155 |  |  |  |  | 160 |  |  |  |  | 165 |
| Asp | Glu | Gln | Leu | Lys | Val | Trp | Asp | Val | Ile | Ala | Arg | Ser | Leu | Ile |
|  |  |  |  | 170 |  |  |  |  | 175 |  |  |  |  | 180 |
| Ile | Asp | Glu | Gly | Glu | Asp | Asp | Leu | Gly | Arg | Gly | Gly | His | Pro | Leu |
|  |  |  |  | 185 |  |  |  |  | 190 |  |  |  |  | 195 |
| Ser | Lys | Ile | Thr | Gly | Asn | Ser | Gly | Glu | Arg | Leu | Ala | Cys | Gly | Ile |
|  |  |  |  | 200 |  |  |  |  | 205 |  |  |  |  | 210 |
| Ile | Ala | Arg | Ser | Ala | Gly | Leu | Phe | Gln | Asn | Pro | Lys | Gln | Ile | Cys |
|  |  |  |  | 215 |  |  |  |  | 220 |  |  |  |  | 225 |
| Ser | Cys | Asp | Gly | Leu | Thr | Ile | Trp | Glu | Glu | Arg | Gly | Arg | Pro | Ile |
|  |  |  |  | 230 |  |  |  |  | 235 |  |  |  |  | 240 |
| Ala | Gly | Lys | Gly | Arg | Lys | Glu | Ser | Ala | Gln | Pro | Pro | Ala | His | Leu |
|  |  |  |  | 245 |  |  |  |  | 250 |  |  |  |  | 255 |

(2) INFORMATION FOR SEQ ID NO:3:

(i) SEQUENCE CHARACTERISTICS:
        (A) LENGTH: 26 BASE PAIRS
        (B) TYPE: NUCLEIC ACID
        (C) STRANDEDNESS: SINGLE
        (D) TOPOLOGY: LINEAR (ii) MOLECULE TYPE: OLIGONUCLEOTIDE (xi) SEQUENCE DESCRIPTION: SEQ ID NO:3:

CGGGATCCAT GGGCAGCGGC CAGTTG                                      26

(2) INFORMATION FOR SEQ ID NO:4:

(i) SEQUENCE CHARACTERISTICS:
        (A) LENGTH: 31 BASE PAIRS
        (B) TYPE: NUCLEIC ACID
        (C) STRANDEDNESS: SINGLE
        (D) TOPOLOGY: LINEAR ( i i ) MOLECULE TYPE: OLIGONUCLEOTIDE ( x i ) SEQUENCE DESCRIPTION: SEQ ID NO:4:

CGTCTAGAGG TCCTGCCTGC TCAAAGGTGG G               31

( 2 ) INFORMATION FOR SEQ ID NO:5:

( i ) SEQUENCE CHARACTERISTICS:
       ( A ) LENGTH: 20 BASE PAIRS
       ( B ) TYPE: NUCLEIC ACID
       ( C ) STRANDEDNESS: SINGLE
       ( D ) TOPOLOGY: LINEAR ( i i ) MOLECULE TYPE: OLIGONUCLEOTIDE ( x i ) SEQUENCE DESCRIPTION: SEQ ID NO:5:

AATTAACCCT CACTAAAGGG               20

( 2 ) INFORMATION FOR SEQ ID NO:6:

( i ) SEQUENCE CHARACTERISTICS:
       ( A ) LENGTH: 57 BASE PAIRS
       ( B ) TYPE: NUCLEIC ACID
       ( C ) STRANDEDNESS: SINGLE
       ( D ) TOPOLOGY: LINEAR ( i i ) MOLECULE TYPE: OLIGONUCLEOTIDE ( x i ) SEQUENCE DESCRIPTION: SEQ ID NO:6:

CGCTCTAGAT CAAGCGTAGT CTGGGACGTC GTATGGGTAA AGGTGGGCAG GGGGCTG               57

( 2 ) INFORMATION FOR SEQ ID NO:7:

( i ) SEQUENCE CHARACTERISTICS:
       ( A ) LENGTH: 78 AMINO ACIDS
       ( B ) TYPE: AMINO ACID
       ( C ) STRANDEDNESS:
       ( D ) TOPOLOGY: LINEAR ( i i ) MOLECULE TYPE: PROTEIN ( x i ) SEQUENCE DESCRIPTION: SEQ ID NO:7:

Met Lys Cys Val Met Thr Thr Ala Gly Lys Lys Thr Glu Asp Asn
                  5                  10                  15

Gly Pro Val His Val His Ala Glu Phe Ser Lys Ala Lys Phe Glu
                 20                  25                  30

Phe Thr Gly Thr Ala Ala Thr Lys Gln Glu Ala Glu Ile Val Val
                 35                  40                  45

Gly Asn Val Tyr Asn Ala Thr Lys Leu Ile Ser Leu Asn Gly Ser
                 50                  55                  60

His Ser Ile Gly Met Val His Asn Glu Val Ala Gly Val Val Gly
                 65                  70                  75

Leu Ala Glu
        78

( 2 ) INFORMATION FOR SEQ ID NO:8:

( i ) SEQUENCE CHARACTERISTICS:
       ( A ) LENGTH: 81 AMINO ACIDS
       ( B ) TYPE: AMINO ACID
       ( C ) STRANDEDNESS:
       ( D ) TOPOLOGY: LINEAR ( i i ) MOLECULE TYPE: PROTEIN ( x i ) SEQUENCE DESCRIPTION: SEQ ID NO:8:

```
Thr Lys Cys Val Lys Asp Pro Gln Thr Ile His Glu Ala Lys Gly
              5                   10                  15

Asp Thr Val Val Val Thr Ser Thr Thr Glu Asp Phe Phe Asn Gln
             20                  25                  30

Gly Thr Ala Pro Leu Ser Lys Lys Lys Glu Glu Val Thr Lys Asn
             35                  40                  45

Val Val Asp Ile Val Pro Leu Ile Ser Leu Ser Gly Glu Tyr Ser
             50                  55                  60

Ile Gly Thr Met Val Val His Lys Pro Asn Glu Glu Thr Lys Ala
             65                  70                  75

Ser Val Gly Ile Ile Lys
             80
```

( 2 ) INFORMATION FOR SEQ ID NO:9:

( i ) SEQUENCE CHARACTERISTICS:
( A ) LENGTH: 84 AMINO ACIDS
( B ) TYPE: AMINO ACID
( C ) STRANDEDNESS:
( D ) TOPOLOGY: LINEAR ( i i ) MOLECULE TYPE: PROTEIN ( x i ) SEQUENCE DESCRIPTION: SEQ ID NO:9:

```
Ala Lys Gly Cys Val Asn Ser Ser Glu Gly Lys Thr Ile Phe Thr
              5                   10                  15

His Glu Gly Asn Gly Ala Thr Thr Val Thr Val Ser Arg Phe Ala
             20                  25                  30

Leu Asn Gly Met Thr Pro Lys Thr Ala Glu Ala Asn Ala Ile Ile
             35                  40                  45

Val Gly Asp Thr Thr Thr Ile Thr Ser Ile Pro Leu Ser Gly Pro
             50                  55                  60

Asn Ser Ile Val Gly Ala Ile Val Val His Ala Asp Pro Lys Glu
             65                  70                  75

Leu Ser Ala Gly Val Gly Ile Gln Gly
             80
```

( 2 ) INFORMATION FOR SEQ ID NO:10:

( i ) SEQUENCE CHARACTERISTICS:
( A ) LENGTH: 90 AMINO ACIDS
( B ) TYPE: AMINO ACID
( C ) STRANDEDNESS:
( D ) TOPOLOGY: LINEAR ( i i ) MOLECULE TYPE: PROTEIN ( x i ) SEQUENCE DESCRIPTION: SEQ ID NO:10:

```
Val Lys Cys Val Ile Asn Asp Ala Lys Thr Phe Glu Glu Ser Ser
              5                   10                  15

Gly Thr Pro Val Lys Val Ser Glu Val Cys Ala Lys Phe Glu Phe
             20                  25                  30

Glu Phe Asn Gly Met Ser Pro Tyr Lys Glu Ala Val Glu Asn Leu
             35                  40                  45

Ile Glu Thr Gly Cys Pro Thr Lys Val Asn Ile Thr Ser Lys Ile
             50                  55                  60

Thr Leu Phe Gly Ala Asp Ser Ile Gly Thr Val Val Val His Ala
             65                  70                  75

Asp Ala Gln Glu Ser Ala Ala Ile Gly Val Gly Ile Ile Lys Val
             80                  85                  90
```

( 2 ) INFORMATION FOR SEQ ID NO:11:

( i ) SEQUENCE CHARACTERISTICS:
    ( A ) LENGTH: 80 AMINO ACIDS
    ( B ) TYPE: AMINO ACID
    ( C ) STRANDEDNESS:
    ( D ) TOPOLOGY: LINEAR ( i i ) MOLECULE TYPE: PROTEIN ( x i ) SEQUENCE DESCRIPTION: SEQ ID NO:11:

```
Thr Lys Cys Val Lys Asp Pro Ile Ile Asn Glu Lys Glu Ser Asn
                 5                   10                  15
Gly Pro Val Lys Val Trp Ser Lys Thr Glu Phe Glu Phe Asn Ala
                20                   25                  30
Gly Thr Ala Pro Leu Ser Arg Lys Lys Glu Glu Val Thr Lys Val
                35                   40                  45
Asp Val Ser Ile Ser Val Ile Ser Leu Ser Gly Asp His Cys Ile
                50                   55                  60
Gly Thr Val Val His Lys Ala Lys Asn Glu Glu Thr Lys Ala Ser
                65                   70                  75
Val Gly Ile Ile Gln
                80
```

( 2 ) INFORMATION FOR SEQ ID NO:12:

( i ) SEQUENCE CHARACTERISTICS:
    ( A ) LENGTH: 82 AMINO ACIDS
    ( B ) TYPE: AMINO ACID
    ( C ) STRANDEDNESS:
    ( D ) TOPOLOGY: LINEAR ( i i ) MOLECULE TYPE: PROTEIN ( x i ) SEQUENCE DESCRIPTION: SEQ ID NO:12:

```
Val Lys Cys Val Asn Ser Ser Glu Gly Ser Thr Tyr Leu Thr Val
                 5                   10                  15
Gly Val Ala Pro Thr Thr Val Asn Asn Ser Lys Phe Ala Leu Asn
                20                   25                  30
Gly Met Thr Pro Tyr Ala Lys Glu Ala Glu Glu Val Val Ile Thr
                35                   40                  45
Val Gly Glu Thr Ser Thr Ile Thr Lys Ile Pro Leu Thr Gly Pro
                50                   55                  60
Gln Ser Ile Gly Ala Val Val Val His Ala Asp Pro Lys Glu Ser
                65                   70                  75
Ala Gly Ile Gly Ile Gln Gly
                80
```

( 2 ) INFORMATION FOR SEQ ID NO:13:

( i ) SEQUENCE CHARACTERISTICS:
    ( A ) LENGTH: 77 AMINO ACIDS
    ( B ) TYPE: AMINO ACID
    ( C ) STRANDEDNESS:
    ( D ) TOPOLOGY: LINEAR ( i i ) MOLECULE TYPE: PROTEIN ( x i ) SEQUENCE DESCRIPTION: SEQ ID NO:13:

```
Val Lys Val Ala Thr Asp Lys Thr Ile Phe Ser Glu Gly Asp Gly
                 5                   10                  15
Pro Thr Thr Val Thr Ser Ser Lys Phe Ala Leu Thr Gly Met Thr
```

```
                              20                         25                          30
Pro Val Lys Glu Ala Glu Glu Ala Thr Gly Glu Val Val Asn Val
                35                          40                         45

Asn Ile Thr Ser Ile Pro Leu Ala Gly Pro His Ser Ile Gly Ala
                50                          55                         60

Val Val Val His Ala Asp Pro Lys Glu Ser Ala Gly Val Gly Ile
                65                          70                         75

Gln Gly
```

( 2 ) INFORMATION FOR SEQ ID NO:14:

( i ) SEQUENCE CHARACTERISTICS:
    ( A ) LENGTH: 80 AMINO ACIDS
    ( B ) TYPE: AMINO ACID
    ( C ) STRANDEDNESS:
    ( D ) TOPOLOGY: LINEAR ( i i ) MOLECULE TYPE: PROTEIN ( x i ) SEQUENCE DESCRIPTION: SEQ ID NO:14:

```
Met Lys Cys Val Lys Asp Pro Thr Ile His Glu Lys Ala Ser Gly
                 5                          10                         15

Glu Pro Trp Lys Ser Gln Thr Thr Glu Gln Phe Asn Gln Gly Thr
                20                          25                         30

Ala Pro His Ser Lys Lys Ala Glu Glu Val Thr Gly Lys Val Asn
                35                          40                         45

Val Ser Ile Arg Val Ile Ser Leu Ser Gly Glu His Ser Ile Gly
                50                          55                         60

Thr Met Val Val His Lys Gln Lys Asn Glu Glu Thr Lys Ala Ser
                65                          70                         75

Val Gly Ile Ile Gln
                80
```

( 2 ) INFORMATION FOR SEQ ID NO:15:

( i ) SEQUENCE CHARACTERISTICS:
    ( A ) LENGTH: 79 AMINO ACIDS
    ( B ) TYPE: AMINO ACID
    ( C ) STRANDEDNESS:
    ( D ) TOPOLOGY: LINEAR ( i i ) MOLECULE TYPE: PROTEIN ( x i ) SEQUENCE DESCRIPTION: SEQ ID NO:15:

```
Val Lys Cys Val Ala Ser Asp Lys Arg Glu Gln Asp Asp Gly Asp
                 5                          10                         15

Val Thr Val Lys Glu Thr Asp Asn Phe Ile Val Phe Asn Gly Leu
                20                          25                         30

Ala Pro Gln Asn Lys Asn Ser Lys Ala Val Thr Glu Gly Val Gln
                35                          40                         45

Asn Phe Thr Pro Ile Ser Leu Lys Gly Glu Arg Ser Ile Gly Thr
                50                          55                         60

Ala Val Val His Lys Gln Lys Asp Asp Glu Leu Lys Ala Gly Val
                65                          70                         75

Gly Phe Cys Pro
```

( 2 ) INFORMATION FOR SEQ ID NO:16:

( i ) SEQUENCE CHARACTERISTICS:
    ( A ) LENGTH: 91 AMINO ACIDS
    ( B ) TYPE: AMINO ACID ( C ) STRANDEDNESS:
( D ) TOPOLOGY: LINEAR ( i i ) MOLECULE TYPE: PROTEIN ( x i ) SEQUENCE DESCRIPTION: SEQ ID NO:16:

```
Val Gln Ala Val Lys Asp Ala Gly Ser Lys Glu Ala Ser Glu Ser
                 5                  10                  15

Glu Pro Thr Thr Val Ser Tyr Glu Ala Asn Ser Asn Ala Glu Arg
                20                  25                  30

Phe Ile Glu Phe Ala Gly Val Ala Pro Phe Lys Lys Thr Ala Thr
                35                  40                  45

Glu Val Val Met Lys Thr Glu Asn Val Lys Gly Ser Phe Lys Ser
                50                  55                  60

Leu Ile Leu Ile Gly Pro Thr Ser Val Gly Val Val His Ala Gln
                65                  70                  75

Lys Asp Thr Glu Glu Leu Lys Ala Pro Pro Val Ile Gly Ile Thr
                80                  85                  90

Asn
```

SUPEROXIDE DISMUTASE-4

This invention relates to newly identified polynucleotides, polypeptides encoded by such polynucleotides, the use of such polynucleotides and polypeptides, as well as the production of such polynucleotides and polypeptides. More particularly, the polypeptide of the present invention is Superoxide Dismutase-4 (SOD-4).

There is a very strong thermodynamic driving force for the reactions between oxygen and biochemical compounds in the body such as proteins, carbohydrates, lipids and nucleic acids. If such reactions go to completion, water, carbon dioxide and a number of waste products are formed as end products with the release of large amounts of energy. Oxidation of biological compounds is the source of energy of living organisms. Such reactions occur spontaneously but are very slow due to reaction barriers. These barriers are overcome by enzymes in intermediary metabolism, and the final reaction with oxygen takes place in the mitochondria, where the oxygen is reduced by four electrons to water without the liberation of any intermediate products. The reaction is accomplished by cytochrome oxidase complex in the electron transport chain and the energy is bound by the formation of ATP.

However, the direct four step reduction of oxygen to water is unique, and when oxygen reacts spontaneously or is catalyzed by enzymes it is forced to react one step at a time. A series of reactive and toxic intermediates are formed, namely the superoxide radical ($O_2^-$), hydrogen peroxide ($H_2O_2$), and the hydroxyl radical ($OH^-$).

Two of these, $O_2^-$ and $OH^-$, have single unpaired electrons and are therefore called free radicals. A few percent of the oxygen consumption in the body has been estimated to lead to the formation of the toxic reduction intermediates, The toxic affects of oxygen are mainly ascribable to the actions of these intermediates, Oxygen in itself reacts slowly with most biochemical compounds, The toxic reactions are in general initiated by processes giving rise to oxygen radicals, which in themselves cause direct damage to biochemical compounds or start chain reactions involving oxygen.

Some compounds react spontaneously with oxygen, i.e., they autoxidize. Virtually all autoxidations result in the formation of toxic oxygen reduction intermediates. Autoxidation of adrenalin, pyrogallol and several other compounds lead to the formation of the superoxide radical. When ionizing radiation passes through an aqueous solution containing oxygen, the superoxide radical is the radical found in the highest concentration. The toxic oxygen reduction products so formed are of fundamental importance for the killing ability of the cells, but may also lead to damage in the surrounding tissue.

Hydrogen peroxide is always formed when superoxide is formed by way of the dismutation reaction. Most oxidases in the body directly reduce oxygen to hydrogen peroxide.

Organisms living in the presence of oxygen have been forced to develop a number of protective mechanisms against the toxic oxygen reduction metabolites. The protective factors include superoxide dismutases (SOD) which dismutate the superoxide radical and are found in relatively constant amounts in mammalian cells and tissue. The best known of these enzymes is CuZnSOD which is a dimer with a molecular weight of 33,000 containing two copper and two zinc atoms. CuZnSOD is found in the cytosol and in the intermembrane space of the mitochondria. MnSOD is a tetramer with a molecular weight of 85,000 containing four Mn atoms, and is mainly located in the mitochondrial matrix. Until recently the extra cellular fluids were assumed to lack SOD activity. However U.S. Pat. No. 5,248,603 recently disclosed the presence of a superoxide dismutase in extracellular fluids (e.g., blood plasma, lymph, synovial fluid and cerebrospinal fluid) which was termed EC-SOD.

Crystallographic structures of recombinant human CuZnSOD have been determined, refined and analyzed at 2.5 A resolution for wild-type and a designed thermal stable double-mutant enzyme (Cys-6 - - - Ala, Cys-111 - - - Ser). There is a helix dipole interaction with a Zn site, and 14 residues form two or more structurally conserved side-chain to main-chain hydrogen bonds that appear critical to active-site architecture, loop confirmation and the increased stability resulting from the Cys-111 - - - Ser mutation. Parge, H. E. et al, Proc. Natl. Acad. Sci. U.S.A., 89:6109–13 (1992).

Mutations in the CuZnSOD gene occur in patients with the fatal neurodegenerative disorder familial amyotrophic lateral sclerosis. Screening of the CuZnSOD coding region revealed that the mutation Ala 4 to Val in exon 1 was the most frequent one, mutations were identified in exons 2, 4 and 5 but not in the active site region formed by exon 3. Thus, defective CuZnSOD is linked to motor neuron death and carries implications for understanding and possible treatment of familial amyotrophic lateral sclerosis. The polypeptide of the present invention, SOD-4, is structurally and functionally related to CuZnSOD.

Japanese Patent No. 4327541 discloses a therapeutic drug for immuno-reactions with organs after transplantation containing the active substance of human CuZnSOD obtained by gene recombination.

Japanese Patent No. 4312533 discloses a composition for treating cerebral ischaemia which comprises recombinant CuZn human SOD and inhibits delayed nerve necrosis accompanying ischaemia.

Japanese Patent No. 4248984 discloses a superoxide dismutase derivative which has a longer half-life in blood than SOD and therefore helps treat various diseases.

European Patent No. 499621 discloses a method for purifying recombinant CuZnSOD and a method for increasing the yield of the B isoform analog of this polypeptide.

Japanese Patent No. 2156884 discloses a 153 amino acid polypeptide having human superoxide dismutase properties and a DNA sequence encoding such polypeptide, a DNA sequence expressed by the nucleic acid sequence and production of the polypeptide by culture of host cells.

Japanese Patent No. 63313581 discloses a pharmacologically active modified superoxide dismutase which is obtained by reacting SOD with a compound containing an amino or carboxyl group.

Japanese Patent No. 63077822 discloses an agent for improving the function of organs which uses a human SOD-like polypeptide as the active substance.

In accordance with one aspect of the present invention, there is provided a novel mature polypeptide which is SOD-4, as well as fragments, analogs and derivatives thereof. The polypeptide of the present invention is of human origin.

In accordance with another aspect of the present invention, there are provided polynucleotides (DNA or RNA) which encode such polypeptides.

In accordance with yet a further aspect of the present invention, there is provided a process for producing such polypeptides by recombinant techniques.

In accordance with yet a further aspect of the present invention, there is provided a process for utilizing such polypeptides, or polynucleotides encoding such polypeptides for therapeutic purposes, for example, for treating inflammatory pathologies, ulcers, arrhythmia, ischaemia, oedema, paraquat intoxication, rheumatoid arthritis and osteoarthritis, reducing reperfusion injuries and decreasing blood pressure.

In accordance with yet a further aspect of the present invention, there is provided an antibody against such polypeptides.

These and other aspects of the present invention should be apparent to those skilled in the art from the teachings herein.

The following drawings are illustrative of embodiments of the invention and are not meant to limit the scope of the invention as encompassed by the claims.

FIG. 1 shows the cDNA sequence and deduced amino acid sequence for the SOD-4 gene. The amino acid sequence encodes for one of the mature forms of the polypeptide, since there are at least two in-frame ATG start codons. The mature polypeptide could start at either one of the ATG codons. The standard one letter abbreviation for amino acids is used.

FIG. 2 displays the amino acid homology between SOD-4 with eleven other cytosolic CuZnSODs from various species. The copper-zinc-bind sites (in boldface type) are formed by six His residues and one Asp residue. The Arg (R) residue is believed necessary to guide the superoxide to the activity site. Identical residues are represented by dashes and deletions are represented by dots.

Figure 3:
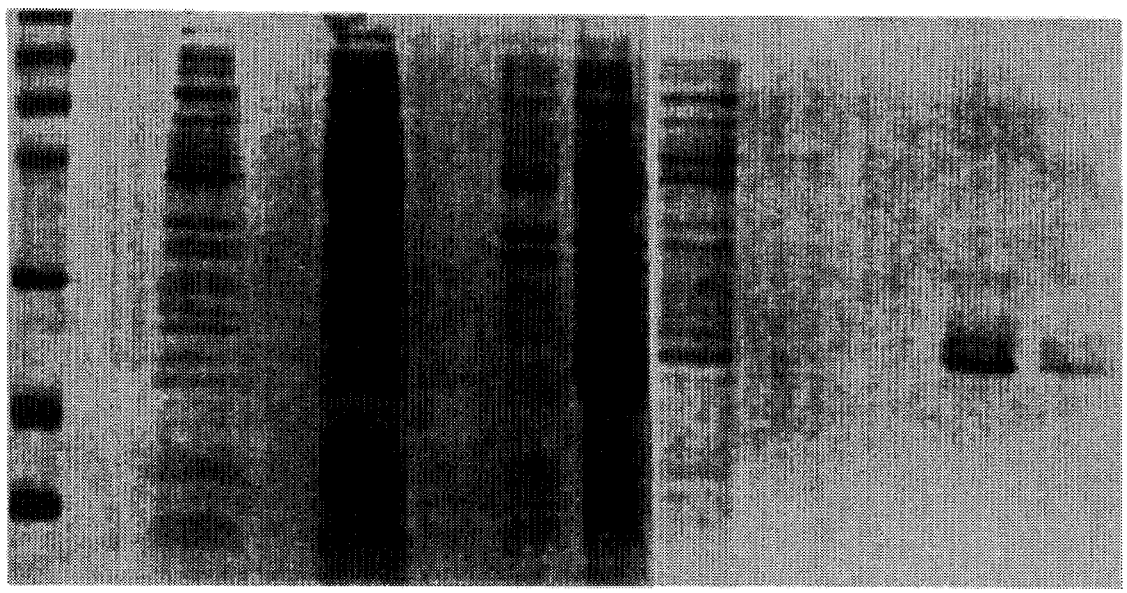
FIG. 3 shows the results of bacterial expression and purification of human SOD-4 after separation on an SDS polyacrylamide gel.

In accordance with an aspect of the present invention, there is provided an isolated nucleic acid (polynucleotide) which encodes for the mature polypeptide having the deduced amino acid sequence of FIG. 1 (SEQ ID NO:2) or for the mature polypeptide encoded by the cDNA of the clone deposited as ATCC Deposit No. 75716 on Mar. 22, 1994.

The polynucleotide of the present invention was isolated from an early stage human brain cDNA library. It contains an open reading frame encoding a polypeptide of 255 amino acids. The polypeptide has the highest degree of homology to CuZnSOD isolated from *Schistosoma mansoni* having 51% identity and 72% similarity over a 151 amino acid overlap.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID NO:1) or that of the deposited clone or may be a different coding sequence which coding sequence, as a result of the redundancy or degeneracy of the genetic code, encodes the same, mature polypeptide as the DNA of FIG. 1 (SEQ ID NO:1) or the deposited cDNA.

The polynucleotide which encodes for the mature polypeptide of FIG. 1 (SEQ ID NO:2) or for the mature polypeptide encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID NO:2) or the polypeptide encoded by the cDNA of the deposited clone. The variant of the polynucleotide may be a naturally occurring allelic variant of the polynucleotide or a nonnaturally occurring variant of the polynucleotide.

Thus, the present invention includes polynucleotides encoding the same mature polypeptide as shown in FIG. 1 (SEQ ID NO:2) or the same mature polypeptide encoded by the cDNA of the deposited clone as well as variants of such polynucleotides which variants encode for a fragment, derivative or analog of the polypeptide of FIG. 1 (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides of the present invention may also have the coding sequence fused in frame to a marker sequence which allows for purification of the polypeptide of the present invention. The marker sequence may be a hexa-histidine tag supplied by a pD10 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 50% and preferably 70% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the cDNA of FIG. 1 (SEQ ID NO:1) or the deposited cDNA.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a SOD-4 polypeptide which has the deduced amino acid sequence of FIG. 1 (SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIG. 1 (SEQ ID NO:2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the SOD-4 genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli*. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli*, Streptomyces, *Salmonella typhimurium*; fungal cells, such as yeast; insect cells such as Drosophila and Sf9; animal cells such as CHO, COS or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., U.S.A.). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. It is preferred to have low concentrations (approximately 0.15–5 mM) of calcium ion present during purification. (Price et al., J. Biol. Chem., 244:917 (1969)). Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

SOD-4 may also be employed as an anti-inflammatory agent. Other SOD proteins have been shown to exhibit an anti-inflammatory affect in a series of animal models of inflammation as well as in inflammatory diseases in animals (Huber et al, eds. Michelson el al, Academic Press, 517–549, (1977). SOD-4 may also be used to treat rheumatoid arthritis and the adverse effects of ionizing radiation since, in humans, positive affects have been shown using SOD proteins to treat rheumatoid arthritis and arthroses as well as adverse affects of treatment with ionizing radiation. The mechanism by which SOD-4 works is by removing oxidation products, which products cause tissue degeneration.

SOD-4 may be used to treat Crohn's disease, Bechet's disease, dermatitis, ulcers, ulcerative colitis, and against the adverse effects of radiation therapy. Other SOD proteins have been found to be effective against these conditions (Niwa, Y et al, Free Rad. Res. Comms. 1:137–153 (1985)).

If the supply of blood to a tissue is cut off, the tissue will slowly become necrotic. Oxygen radicals formed as a result of the reappearance of oxygen in previously ischaemic tissue appear to contribute to the damage. Thus the removal of these free radicals by SOD-4 helps to protect tissue against damage. SOD-4 may be employed to reduce the incidence of ischaemia and reperfusion induced arrhythmias by a similar mechanism, since SOD proteins have been reported to affect these conditions (Woodward, B. et al, J. Mol. Cell. Cardiol. 17:485–493 (1985). In the same manner, SOD-4 may be employed to treat cerebral ischaemia and kidney ischaemia, SOD proteins have been demonstrated to protect tissues in ischaemia or anoxiareperfusion models in the kidney (Baker, G. L., et al., Am. Surg., 202:628–41 (1985).

Also, SOD-4 may be employed in connection with kidney transplantations and other organ transplantations such as skin, lung, liver and pancreas.

SOD-4 may be employed to treat burns. The local oedema after an experimental slight burn in rats could be somewhat decreased through injection of SOD proteins (Bjork and Artursson, Burns, 9:249–256 (1983).

Parenterally administered CuZnSOD has been reported to prevent bronchopulmonary dysplasia in preterm neonates suffering from infantile respiratory distress. The CuZnSOD has recently received orphan drug status for this treatment. Accordingly, SOD-4 may also be employed to treat these diseases also. (Rosenfeld W. et al, J. Pediatr. 105:781–785 (1984).

In various types of autoimmune diseases, such as systemic lupus erythematosus, and rheumatoid arthritis an increased frequency of chromosomal breaks in lymphocytes has been demonstrated. Plasma from such patients contains a chromosome breaking factor, called clastogenic factor. Superoxide radicals in the plasma results in formation of this factor. SOD-4 may protect against this clastogenic activity by removing the superoxide radicals.

Superoxide radicals tend to damage cells, DNA and proteins by oxidative stress which may disrupt the normal cell cycle and lead to uncontrolled division of cells which is the basis of a cancer. Accordingly, SOD-4 can be employed to prevent or control cancer by the removal of superoxide radicals from a patient's system.

Oxygen radicals contribute to the damaging affects of a number of toxic substances such as paraquat and alloxan. SOD-4 may protect against these toxic substances through direct injection.

Alloxan has been reported to have diabetogenic activity. SOD-4 may protect against this diabetogenic activity of alloxan in vivo. Beta-cells of the pancreas are extremely sensitive to alloxan, and this sensitivity may lead to insulin-dependent diabetes mellitus. It may therefore be contemplated to protect the Beta cells with injections with SOD-4 at the first onset of diabetes mellitus.

The polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

The polypeptides of the present invention may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. The amounts and dosage regimens of SOD-4 administered to a subject will depend on a number of factors such as the mode of administration, the nature of the condition being treated and the judgment of the prescribing physician. Generally speaking, they are given, for example, in therapeutically effective doses of at least about 10 µg/kg body weight and in most cases they will be administered in an amount not in excess of about 8 mg/Kg body weight per day and preferably the dosage is from about 10 µg/kg to about 1 mg/kg body weight daily, taking into account the routes of administration, symptoms, etc.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clones to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clones from which the EST was derived, and the longer the better. For example, 2,000 bp is good, 4,000 is better, and more than 4,000 is probably not necessary to get good results a reasonable percentage of the time. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Comparison of affected and unaffected individuals generally involves first looking for structural alterations in the chromosomes, such as deletions or translocations that are visible from chromosome spreads or detectable using PCR based on that cDNA sequence. Ultimately, complete sequencing of genes from several individuals is required to confirm the presence of a mutation and to distinguish mutations from polymorphisms.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention.

Antibodies against SOD-4 may be used as a diagnostic to detect deficiencies in the coding sequence of SOD-4 which are associated with familial amyotrophic lateral sclerosis. Accordingly, an antibody against SOD-4, preferably monoclonal antibodies, could detect the presence of the mutated form of the SOD-4 gene and, therefore, would be predictive of the familial amyotrophic lateral sclerosis disease.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of SOD-4

The DNA sequence encoding for SOD-4, ATCC #75716 is initially amplified using PCR oligonucleotide primers corresponding to the 5' and 3' sequences of the processed SOD-4 protein (minus the signal peptide sequence) and the vector sequences 3' to the SOD-4 gene. Additional nucleotides corresponding to SOD-4 are added to the 5' and 3' sequences respectively. The 5' oligonucleotide primer has the sequence 5'-CGGGATCCATGGGCAGCGGC-CAGTTG-3' (SEQ ID NO:3) and contains a Bam HI restriction enzyme site followed by 18 nucleotides of SOD-4 coding sequence starting from one of the presumed terminal amino acids of the processed protein. The 3' sequence, 5'-CGTCTAGAGGTCCTGCTCAAAGGTGGG-3' (SEQ ID NO:4) contains complementary sequences to an Xba I restriction site and the last 21 nucleotides of SOD-4 and to a pD10 vector sequence located 3' to the SOD-4 DNA insert. The restriction enzyme sites correspond to the restriction enzyme sites on the bacterial expression vector pD10 (Qiagen, Inc. 9259 Eton Avenue, Chatsworth, Calif., 91311). pD10 encodes antibiotic resistance (Amp$^r$), a bacterial origin of replication (ori), an IPTG-regulatable promoter operator (P/O), a ribosome binding site (RBS), a 6-His tag and restriction enzyme sites. pD10 was then digested with Bam HI and Xba I. The amplified sequences were ligated into pD10 and were inserted in frame with the sequence encoding for the histidine tag and the RBS. The ligation mixture was then used to transform E. coli strain M15/rep4 available from Qiagen under the trademark M15/rep 4 by the procedure described in Sambrook, J et al., Molecular Cloning: A Laboratory Manual, Cold Spring Laboratory Press, 1989. M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized SOD-4 was purified from this solution by chromatography on a Nickel-Chelate column under conditions that allow for tight binding by proteins containing the 6-His tag. Hochuli, E. et al., J. Chromatography 411:177–184 (1984). Proteins from different stages of purification were separated on a 12.5% SDS polyacrylamide gel and stained with Coomassie blue dye. M represents a molecular sizing marker. Lanes 1 and 2 are total extracts from bacteria containing the vector pD10 in the absence (lane 1) and presence (lane 2) of IPTG. Lanes 3 and 4 are total extracts from bacteria containing the expression plasmid pD10-SOD-4 in the absence (lane 3) and presence (lane 4) of IPTG. Lanes 5 through 9 represent elution fractions from a Nickel-Chelate column. Lane 5 is flow-through; lanes 6 and 7 represent elution fractions washed with 6M guanidine HCl, 50 mM NaPO$_4$, pH 8 and pH 6; lanes 8 and 9 are elution fractions washed with 6M guanidine HCl 50 mM NaPO$_4$ pH 5 and pH 2. See FIG. 3.

EXAMPLE 2

Expression of Recombinant SOD-4 in COS cells

The expression of plasmid, pSOD-4-HA is derived from a vector pcDNAI/Amp (Invitrogen) containing: 1) SV40 origin of replication, 2) ampicillin resistance gene, 3) E. coli replication origin, 4) CMV promoter followed by a polylinker region, a SV40 intron and polyadenylation site. A DNA fragment encoding the entire SOD-4 precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to our target protein allows easy detection of the recombinant protein with an antibody that recognizes the HA epitope.

Figure 4:
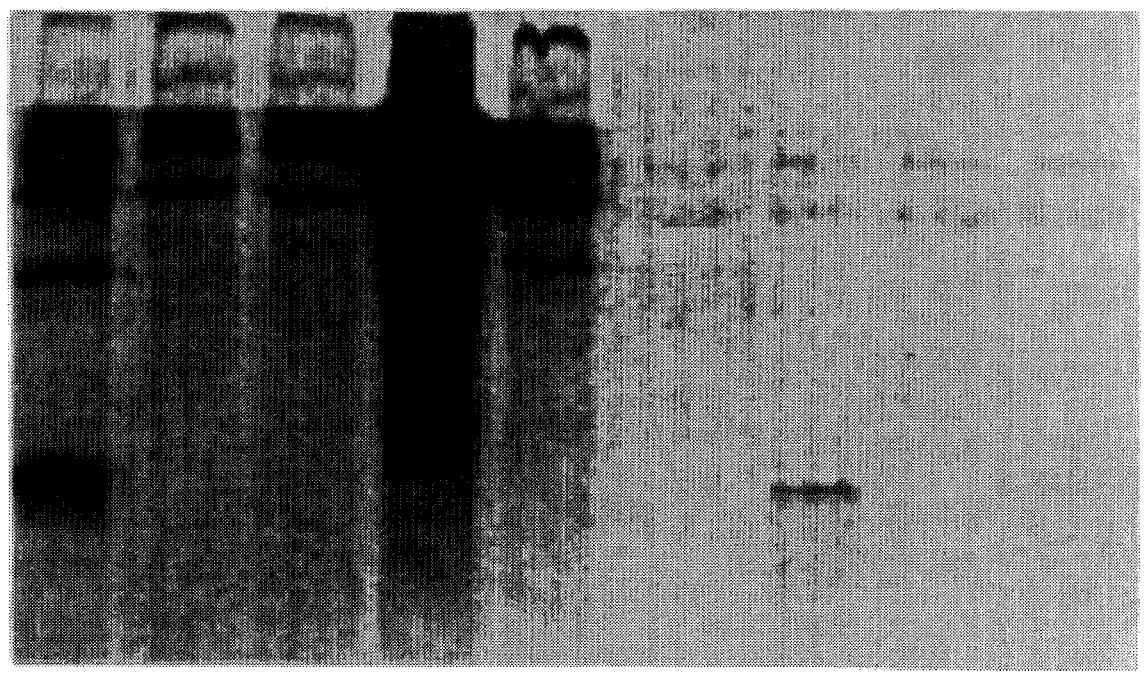
FIG. 4 shows the results of expression of recombinant SOD-4 in COS cells after separation on an SDS polyacrylamide gel.

The plasmid construction strategy is described as follows:

The DNA sequence encoding for SOD-4, ATCC #75716 was constructed by PCR using two primers: the 5' primer sequence 5' -AATTAACCCTCACTAAAGGG-3' (SEQ ID NO:5) in pBluescript vector; the 3' sequence 5' -CGCTCTA-GATCAAGCGTAGTCTGGGACGTCG-TATGGGTAAAGGTGGGCAGGGGGCTG-3' (SEQ ID NO:6) contains complementary sequences to an Xba I restriction enzyme site, translation stop codon, HA tag and the last 18 nucleotides of the SOD-4 coding sequence (not including the stop codon). Therefore, the PCR product contains a Bam HI site from the pBluescript vector, SOD-4 coding sequence followed by HA tag fused in frame, a translation termination stop codon next to the HA tag, and an Xba I site. The PCR amplified DNA fragment and the vector, pBluescript, were digested with Bam HI and Xba I restriction enzymes and ligated. The ligation mixture was transformed into E. coli strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant SOD-4, COS cells were transfected with the expression vector by DEAE-DEXTRAN method. (J. Sambrook, E. Fritsch, T. Maniatis, Molecular Cloning: A Laboratory Manual, Cold Spring Laboratory Press, (1989)). The expression of the SOD-4-HA protein was detected by radiolabelling and immunoprecipitation method. (E. Harlow, D. Lane, Antibodies: A Laboratory Manual, Cold Spring Harbor Laboratory Press, (1988)). Proteins were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5). (Wilson, I. et al., Id. 37:767 (1984)). $^{35}$S-cysteine labeled proteins from COS cell lysates and supernatants were immunoprecipitated with an HA polyclonal antibody and separated using 15% SDS-PAGE. M equals molecular weight markers. Lanes 1 through 4 are cell lysates. Lanes 5 through 8 are supernatants. Lanes 1 and 5 are mock controls with no DNA. Lanes 2 and 6 are MIP-1γ control for secreted proteins. Lanes 3 and 7 are control for cell lysate and lanes 4 and 8 are SOD-4. See FIG. 4.

Numerous modifications and variations of the present invention are possible in light of the above teachings and, therefore, within the scope of the appended claims, the invention may be practiced otherwise than as particularly described.

What is claimed is:

1. An isolated polynucleotide comprising a member selected from the group consisting of:
   (a) a polynucleotide encoding a polypeptide comprising amino acid 1 to amino acid 255 as set forth in SEQ ID NO:2; and
   (b) a polynucleotide which hybridizes to and which is at least 95% complementary to the polynucleotide of (a).

2. The polynucleotide of claim 1 comprising the polynucleotide of (a).

3. The polynucleotide of claim 2 comprising nucleotide 1 to nucleotide 1080 of SEQ ID NO:1.

4. The polynucleotide of claim 1 comprising polynucleotide (b).

5. The polynucleotide of claim 2 wherein the polynucleotide is DNA.

6. The polynucleotide of claim 2 wherein the polynucleotide is RNA.

7. The polynucleotide of claim 3 wherein the polynucleotide is DNA.

8. The polynucleotide of claim 3 wherein the polynucleotide is RNA.

9. An isolated polynucleotide comprising a member selected from the group consisting
   (a) a polynucleotide encoding a polypeptide comprising amino acid 31 to amino acid 255 as set forth in SEQ ID NO:2; and
   (b) a polynucleotide which hybridizes to and which is at least 95% complementary to the polynucleotide of (a).

10. The polynucleotide of claim 9 comprising polynucleotide (a).

11. The polynucleotide of claim 10 comprising nucleotide 115 to nucleotide 879 of SEQ ID NO:1, 12. The polynucleotide of claim 9 comprising polynucleotide (b).

13. The polynucleotide of claim 10 wherein the polynucleotide is DNA.

14. The polynucleotide of claim 10 wherein the polynucleotide is RNA.

15. The polynucleotide of claim 11 wherein the polynucleotide is DNA.

16. The polynucleotide of claim 11 wherein the polynucleotide is RNA.

17. An isolated polynucleotide comprising a member selected from the group consisting of:
   (a) a polynucleotide encoding a mature polypeptide encoded by the SOD-4 polynucleotide contained in ATCC Deposit No. 75716; and
   (b) a polynucleotide which hybridizes to and which is at least 95% complementary to the polynucleotide of (a).

18. The polynucleotide of claim 17 wherein said polynucleotide comprises polypeptide (a) .

19. The polynucleotide of claim 17 wherein said polynucleotide comprises the SOD-4 polynucleotide contained in ATCC Deposit No. 75716, encoding a mature polypeptide.

20. An isolated polynucleotide comprising a member selected from the group consisting of:
   (a) a polynucleotide encoding the polypeptide expressed by the SOD-4 polynucleotide contained in ATCC Deposit No. 75716; and
   (b) a polynucleotide which hybridizes to and which is at least 95% complementary to the polynucleotide of (a).

21. The polynucleotide of claim 20 wherein said polynucleotide comprises polynucleotide (a).

22. The polynucleotide of claim 20 wherein said polynucleotide comprises the SOD-4 polynucleotide contained in ATCC Deposit No. 75716.

23. A vector containing the polynucleotide of claim 2 wherein said polynucleotide is DNA.

24. A vector containing the polynucleotide of claim 3 wherein said polynucleotide in DNA.

25. A vector containing the polynucleotide of claim 4 wherein said polynucleotide is DNA.

26. A vector containing the polynucleotide of claim 10 wherein said polynucleotide is DNA.

27. A vector containing the polynucleotide of claim 11 wherein said polynucleotide is DNA.

28. A vector containing the polynucleotide of claim 18 wherein said polynucleotide in DNA.

29. A vector containing the polynucleotide of claim 21 wherein said polynucleotide is DNA.

30. A host cell transformed or transfected with the vector of claim 23.

31. A host call transformed or transfected with the vector of claim 24.

32. A host cell transformed or transfected with the vector of claim 25.

33. A host cell transformed or transfected with the vector of claim 26.

34. A host cell transformed or transfected with the vector of claim 27.

35. A host cell transformed or transfected with the vector of claim 28.

36. A host cell transformed or transfected with the vector of claim 29.

* * * * *

UNITED STATES PATENT AND TRADEMARK OFFICE
CERTIFICATE OF CORRECTION

PATENT NO. : 5,506,133
DATED : Apr. 9, 1996
INVENTOR(S) : Gu-Liang Yu, et al

It is certified that error appears in the above-identified patent and that said Letters Patent is hereby corrected as shown below:

On title page,

Item [75] Inventors: Guo-Liang Yu, Darnestown; Craig A. Rosen, Laytonsville; Claire M. Fraser, Queenstown; Jeannine D. Gocayne, Silver Spring, all of Md.

Signed and Sealed this

Nineteenth Day of May, 1998

Attest:

BRUCE LEHMAN

*Attesting Officer*  Commissioner of Patents and Trademarks